US007220964B1

(12) United States Patent
Gao et al.

(10) Patent No.: US 7,220,964 B1
(45) Date of Patent: May 22, 2007

(54) FILM THICKNESS AND COMPOSITION MEASUREMENT VIA AUGER ELECTRON SPECTROSCOPY AND ELECTRON PROBE MICROANALYSIS

(75) Inventors: Ying Gao, Santa Clara, CA (US); Gary Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 13 days.

(21) Appl. No.: 11/132,152

(22) Filed: May 18, 2005

(51) Int. Cl.
*G01N 23/00* (2006.01)
(52) U.S. Cl. .................. 250/310; 250/305; 250/307; 250/311; 250/288; 378/46; 378/45; 324/751
(58) Field of Classification Search .............. None
See application file for complete search history.

(56) References Cited

U.S. PATENT DOCUMENTS 6,627,886 B1 * 9/2003 Shachal et al. ............. 250/310
6,781,126 B2 * 8/2004 Kadyshevitch et al. ..... 250/310
6,787,773 B1 * 9/2004 Lee ............................ 250/311

OTHER PUBLICATIONS

Powell, Characterization of Thin Films on Nanometer Scale by Auger Electron Sprectroscopy and X-Ray Photoelectorn Spectroscopy, Applied Surface Science 239 (2005), pp. 470-480.

Heinrich, Electron Probe Quantitation, Chemical Science and Technology Labratory, national Institue of Standards and Technology, Gaithersburg, MD (1991).
Baro,Algorithm for Monte Carlo Simulation of Penetration and Energy Loss of Electrons and Positrons in Matter,Nuclear Instruments and Methods in Physics Research B 100 (1995).
Werner, Partial Intensity Analysis (PIA) for Quantitative Electron Spectroscopy, Surface and Interface Analysis, vol. 23, pp. 737-752 (1995).
Press, Numerical Recipes in C, The Art of Scientific Computing, Second Eddition, pp. 657-659 and 671-675 (1992).

* cited by examiner

*Primary Examiner*—Jack Berman
*Assistant Examiner*—Zia R. Hashmi
(74) *Attorney, Agent, or Firm*—Caven & Aghevli LLC

(57) ABSTRACT

In various embodiments, techniques are described for combining an X-ray detector (e.g., for providing EPMA) and an electron detector (e.g., for providing AES) to provide a tool for determining film compositions and thicknesses on a specimen, such as a semiconductor structure or wafer. In one embodiment, a system includes a beam generator configurable to direct an electron beam towards a specimen. The electron beam may generate Auger electrons and X-rays. The system may also include at least one electron detector disposed adjacent to (e.g., above) the specimen to detect electrons and measure their energies emanating from a top layer of the specimen. One or more X-ray detectors may be disposed adjacent to the specimen to detect X-rays.

23 Claims, 4 Drawing Sheets

FILM THICKNESS AND COMPOSITION MEASUREMENT VIA AUGER ELECTRON SPECTROSCOPY AND ELECTRON PROBE MICROANALYSIS

BACKGROUND

The subject matter described herein generally relates to semiconductors. In one embodiment, techniques described herein provide composition and film thickness information on production semiconductor wafers.

Due to the decreasing size of semiconductor device dimensions, film stack structures have become more complicated to produce and are frequently composed of newer materials. Thus, it has become important to monitor both film thickness and composition during production.

Auger Electron Spectroscopy (AES) and Electron Probe Micro Analysis (EPMA) have been used for film thickness and composition measurement. AES is generally a surface sensitive technique and is usually used for ultra-thin film analysis. Because of the short mean free path of Auger electrons, AES may not be a practical technique for analysis of films thicker than 100 Å. In addition, Auger electron emission probability decreases with atomic number (FIG. 1). Hence, AES has a reduced signal-to-noise ratio (S/N) for heavy element composition analysis.

Furthermore, since X-rays may escape from larger depths in solids than Auger electrons, EPMA may be used to measure films up to about 1 µM thick. However, EPMA may have poor S/N for light elements, such as Boron, Nitrogen, Oxygen, Carbon, Fluorine, and Phosphorus, because of the low X-ray fluorescent yield for light elements (FIG. 1). A long acquisition time may be needed to obtain reasonable precision for light element measurements, which is not preferable for in-line production monitoring. In many cases, it may be difficult for EPMA to be used to determine film composition, if the film layer being tested contains the same element as other layers within the stack. Although double or multiple landing energy methods may help to solve this problem, these methods may suffer from other disadvantages, such as slow measurements, instability of electron beam, and difficulty in accurate control of electron and solid interaction volume.

SUMMARY

In various embodiments, the present invention provides techniques for combining an X-ray detector (e.g., for providing EPMA) and an electron detector (e.g., for providing AES) to create a tool for determining film compositions and thicknesses on a specimen, such as a semiconductor structure or wafer.

In one embodiment of the invention, a system is provided for determining film stack characteristics of a specimen. The system includes a beam generator configurable to direct an electron beam towards a specimen, the electron beam may generate Auger electrons and X-rays to emanate from the specimen. The system also includes at least one electron detector disposed adjacent to (e.g., above) the specimen. The electron detector may be configured to detect electrons and measure their energies emanating from a top layer of the specimen (especially for light elements in one embodiment). One or more X-ray detectors are disposed adjacent to the specimen. The X-ray detector may be configured to detect X-rays having one or more characteristic energies for the heavy elements from a top layer and/or in an underlying layer that lies beneath the top layer.

In another embodiment of the invention, a method is provided for measuring at least one characteristic of a film stack on a specimen. The method includes directing an electron beam towards a specimen such that, the incident electron beam causes X-rays and Auger electrons to emanate from the specimen; detecting Auger electrons at an emission level for a first layer of the film stack; detecting characteristic X-rays at an emission level for a second layer of the film stack; and processing detection data resulting from the detected X-rays and electrons.

Additional advantages, objects and features of embodiments of the invention are set forth in part in the detailed description which follows. It is to be understood that both the foregoing general description and the following detailed description are merely exemplary of embodiments of the invention, and are intended to provide an overview or framework for understanding the nature and character of embodiments of the invention.

BRIEF DESCRIPTION OF THE DRAWINGS

The accompanying drawings are included to provide further understanding of embodiments of the invention, illustrate various embodiments of the invention, and together with the description serve to explain the principles and operation of the invention. In the figures, the left-most digit(s) of a reference number identifies the figure in which the reference number first appears. The use of the same reference numbers in different figures indicates similar or identical items.

DETAILED DESCRIPTION

In the following description, numerous specific details are set forth in order to provide a thorough understanding of embodiments of the present invention. Embodiments of the present invention may be practiced without some or all of these specific details. In other instances, well known process operations have not been described in detail in order not to unnecessarily obscure the present invention.

Also, reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Figure 1:
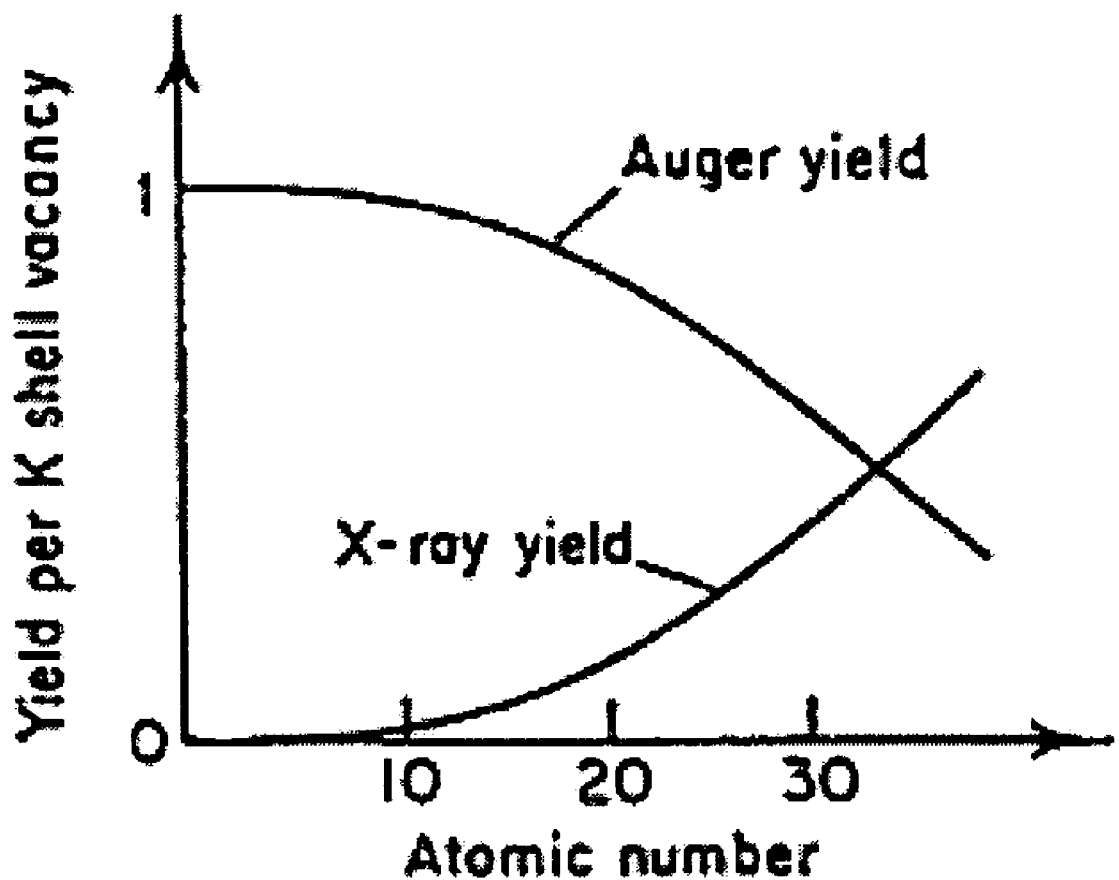
FIG. 1 is a graph of the relative probability of Auger electron emission and X-ray emission from an atom that has had a k-shell electron removed.
Figure 2:
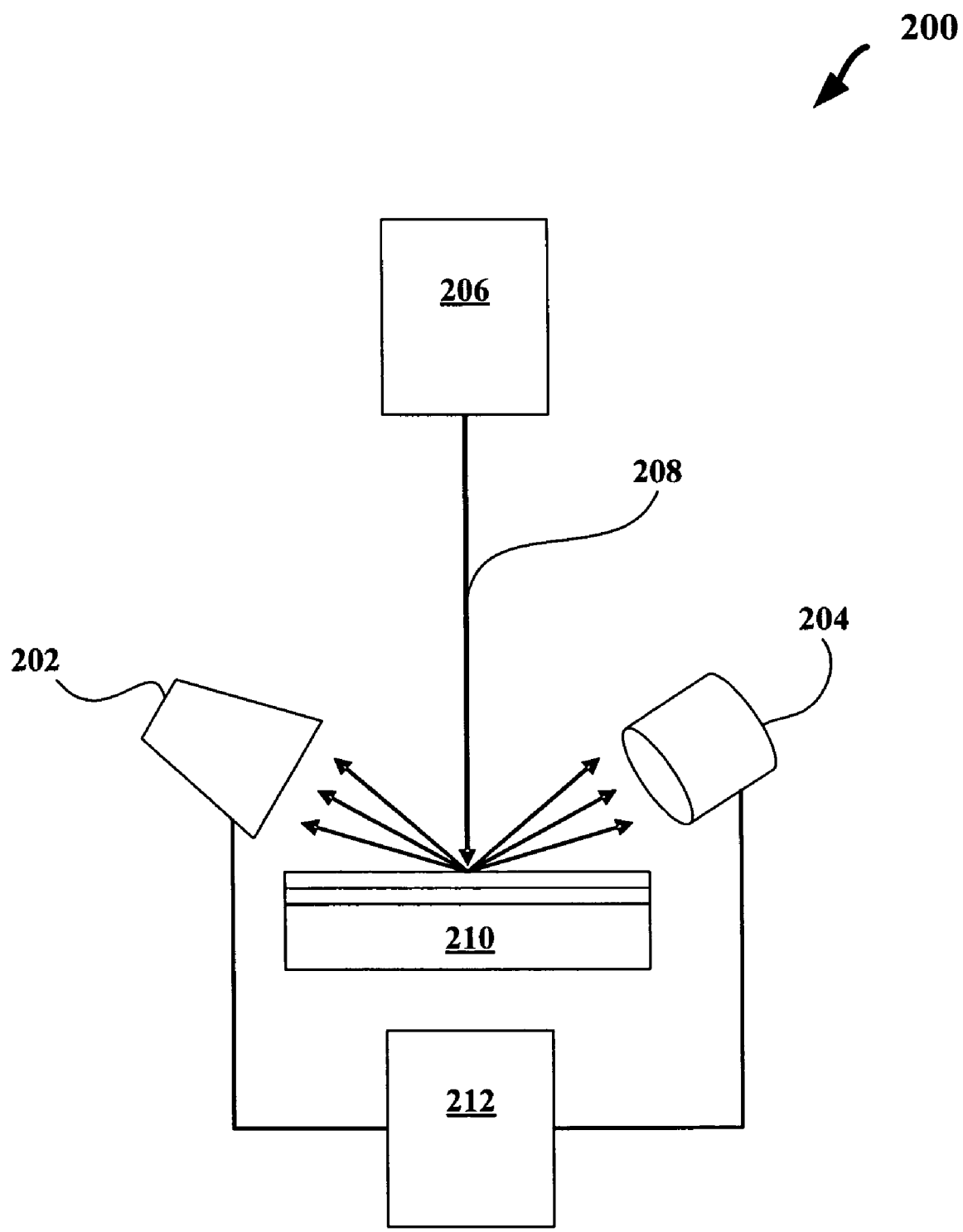
FIG. 2 is a schematic illustration of a film analysis system combining an X-ray detector and an electron detector in accordance with an embodiment of the present invention.

FIG. 2 is a schematic illustration of film analysis system 200 including an X-ray detector 202 and an electron detector 204 in accordance with an embodiment of the present invention. Analysis system 200 also includes a beam generator 206, which directs a charged particle beam 208 at a specimen 210. In one embodiment, a spot size of system 200 is approximately 10 microns in diameter. However, the spot size may range between 0.001 to 100 microns in diameter.

In one embodiment, specimen 210 is a multi-layered semiconductor device or wafer for which layer thickness and composition measurements are desired.

In one embodiment, X-ray detector 202 and electron detector 204 are positioned adjacent specimen 210 to collect X-ray photons and electrons, such as Auger electrons, emanating or emitted from specimen 210. In one embodiment, each of the detectors 202 and 204 may be coupled with an analysis unit 212. Analysis unit 212 may be configured to analyze the data collected by the detectors 202 and 204 and to generate useful information concerning individual film stack layers on specimen 210. The analysis unit may take the form of any suitable processing or computing system, such as a workstation.

X-ray detector 202 detects X-rays from the X-ray region of the electromagnetic spectrum that is associated with specimen 210 so as to gain information regarding the specimen. The X-ray region of the electromagnetic spectrum may include frequencies that range from $2.0 \times 10^{16}$ Hz to $2.0 \times 10^{19}$ Hz. The X-ray analysis may be performed by bombarding specimen 210 with electrically charged particles, such as from electron beam 208, which have sufficient energy to cause X-ray photons to be emitted from specimen 210. By counting the emitted photons at one or more energies, the composition and thickness of specimen 210, which may be, for example, a semiconductor device, may be determined.

The composition of a material may be determined since the specific energies of X-ray photons emitted from such material are related to the material's composition. For example, the thickness of a layer may be determined by counting the number of X-ray photons detected with energies within a narrow range centered on the characteristic energy emission level of the element making up the layer. The total count taken may be directly proportional to the thickness of the conductive layer. The actual thickness of the layer may be then determined by applying a calibration factor, which may be specific to each type of material being measured, to the count data.

In one embodiment, the electron detector 204 measures the energy spectra of characteristic electrons, referred to as Auger electrons, which emanate or are emitted from specimen 210 as it is irradiated by an energetic ionizing beam, such as electron beam 208. Beam 208 causes ionization of atomic core levels in the solid. The resulting core-level vacancy may be immediately filled by another electron from a higher energy level in a radiationless process. The energy released by the transition of the electron from the higher level to the core level may be transferred to another electron in the same level or in another level, enabling this latter electron—the Auger electron—to escape from the atom. The kinetic energy of the Auger electron may be determined by the work function of the atom and the structure of its energy levels.

Because of the nature of the Auger process, each element (except hydrogen and helium) is generally characterized by a unique Auger spectrum, with well-defined energy peaks. By analyzing the distribution and amplitudes of the lines in the Auger spectrum of a given material, the elemental components of the material and their relative concentrations may be determined.

Moreover, the Auger electrons created by the incident ionizing beam escape from the sample in order to be detected and analyzed. After the Auger electrons break free of their host atoms, however, they may rapidly undergo energy losses due to collisions and other phenomena. In solid materials, the mean free paths of Auger electrons may be on the order of 0.4 to 5 nm. Therefore, the Auger electrons created very near the surface of the specimen under study may have a significant probability of escaping without losing energy (and being detected with their characteristic energy).

In one embodiment, Auger electron detector 204 may be configured as a cylindrical mirror analyzer (CMA), which is commercially available from Staib Instruments GmbH (Munich, Germany). Alternatively, other types of electron analyzers may be used for Auger analysis, such as a Cylindrical Sector Analyzer (CSA) with a channeltron detector, available commercially from Focus GmbH (Hunstetten-Gorsroth, Germany), or a hemispherical analyzer (HSA), available from Thermo Electron Corp.

Used in combination, X-ray detector 202 and electron detector 204 provide complementary advantages. For example, electron detector 204 may be capable of high Auger electron yield for light elements and may provide large solid angles to collect the electrons, which makes it a high efficiency detection scheme and suitable for high speed and high precision measurement. In addition, electron detector 204 provides high energy resolution of electron spectra that may distinguish the overlapping peaks in X-ray spectra. Chemical shift information relating to the chemical state of the atoms in the layer may also be obtained because of the higher resolution of electron spectra. The X-ray detector 202 provides heavy element measurement and information from larger depths of the sample. Thus, the combination of X-ray detector 202 and electron detector 204 may achieve relatively optimum measurement for elements, resulting in a faster and higher precision metrology system.

Beam generator 206 may be any suitable device that directs charged particles towards specimen 210, and which, in turn, causes X-rays and Auger electrons to emanate from specimen 210. For example, beam generator 206 may include an electron gun which includes Tungsten and Lanthanum Hexaboride filaments as well as field emission guns. Beam generator 206 is capable of projecting the charged particles with sufficient energy to penetrate at least one layer on specimen 210.

In one embodiment, a conductive layer and a liner layer may be two of the film stack layers penetrated by beam generator 206. The particles may penetrate substantially through the entire conductive and liner layers so as to cause X-rays and Auger electrons to emanate from the entire width of the respective layers. As a result, X-ray and Auger electron measurements from the entire thickness of the penetrated layers may then be taken. By way of example, beam generator 206 may take the form of a scanning electron microscope (SEM) or similar device.

Figure 3:
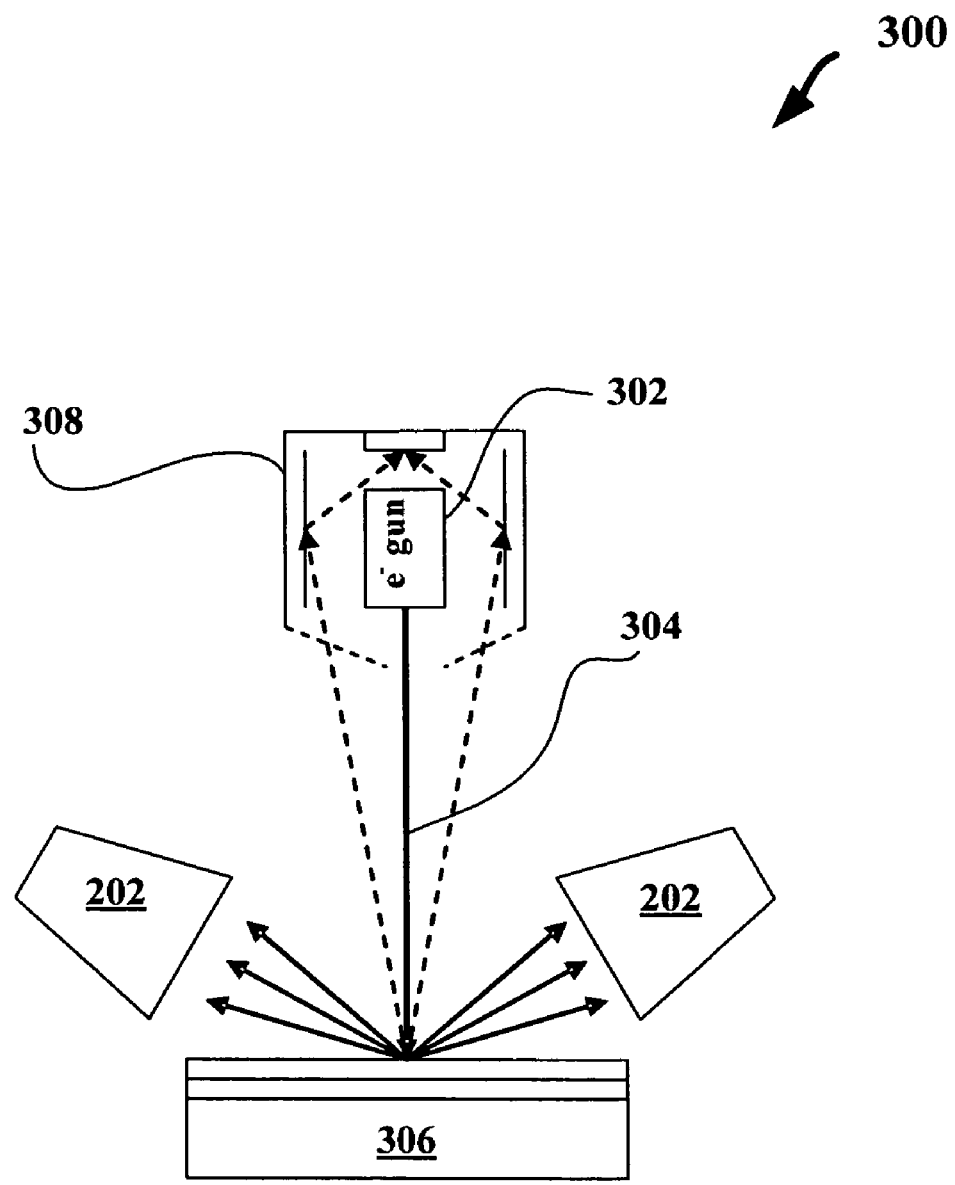
FIG. 3 is a schematic illustration of a coaxial electron detection scheme with multiple detectors in accordance with an embodiment of the present invention.

FIG. 3 is a schematic illustration of a coaxial electron detection scheme with multiple detectors in accordance with an embodiment of the present invention. In one embodiment, an analysis tool 300 comprises a coaxial electron gun 302, which directs a beam 304 of electrons toward a point on the surface of specimen 306, an electron spectrometer 308 for collecting electrons emitted from the specimen surface and one or more X-ray detectors 202 positioned adjacent specimen 306 for collecting X-rays emanating from the specimen surface. Electron beam 304 may be focused to a tight spot on the specimen surface, with a spot diameter that may be no more than about 0.001–30 μm in diameter. In accordance with an embodiment of the present invention, the tight focus of the electron beam may be useful because it allows measurement of films at precise locations on the specimen surface. Accordingly, the electron energy of electron gun 302 may be in the range of 0.5 to 300 keV, with narrow energy spread (<10 eV) and beam current in the range of 0.1 nA to 300 µA.

In one embodiment, electrons scattered from specimen 306 are collected through electron spectrometer 308 having an electron detector, such as an electron counting detector. Spectrometer 308 may provide a count of the number of electrons emitted from specimen 306 as a function of electron energy.

In one embodiment, X-ray detector(s) 202 detects X-rays from the X-ray region of the electromagnetic spectrum that is associated with specimen 306. The X-ray region of the electromagnetic spectrum may include frequencies that range from $2.0 \times 10^{16}$ Hz to $2.0 \times 10^{19}$ Hz. Specimen 306 may be bombarded with electrons from electron gun 302, which may have sufficient energy to cause X-ray photons to be emitted from the specimen. By counting the emitted photons at one or more energy levels, the composition and thickness of specimen 306 may be determined.

Figure 4:
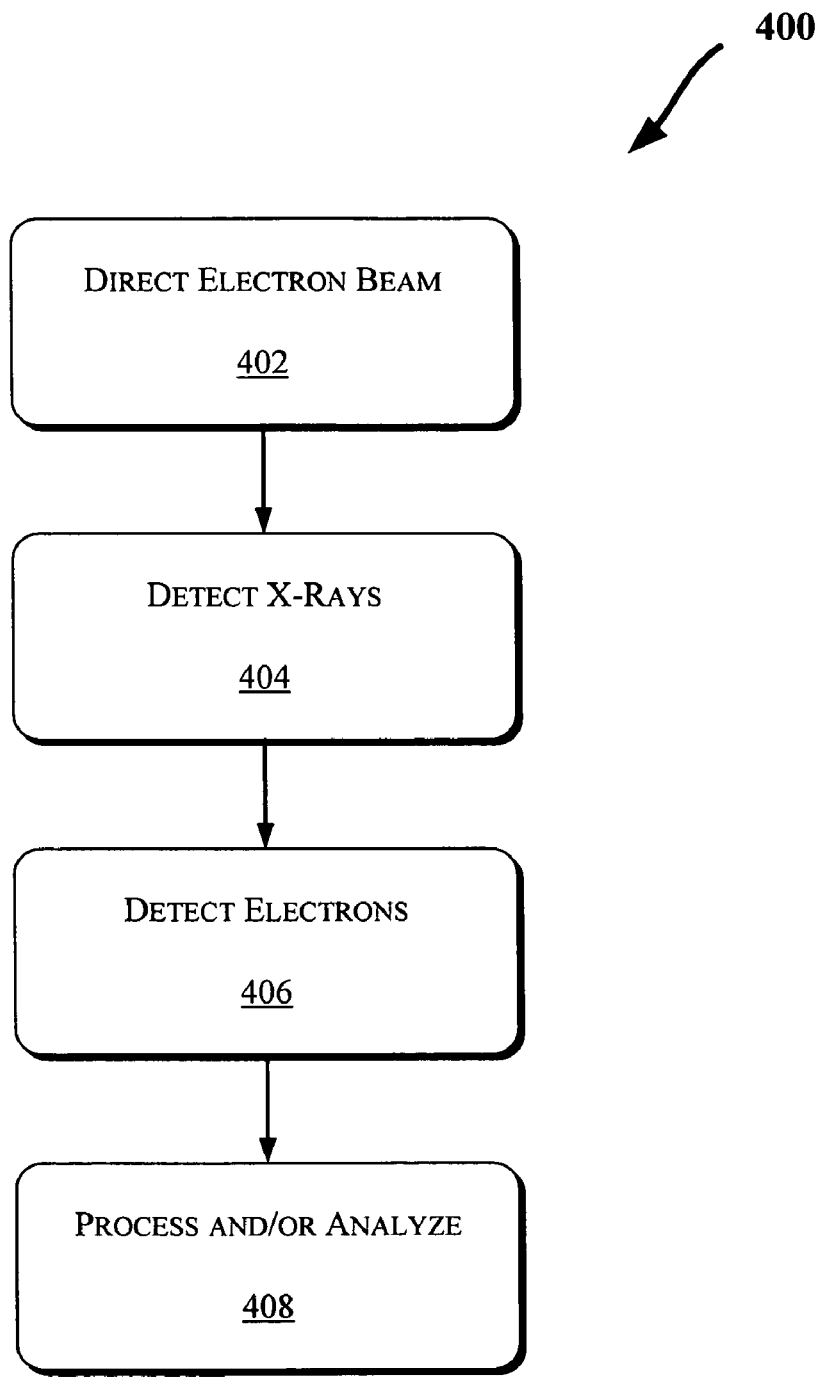
FIG. 4 is a flowchart illustrating a method of the present invention in accordance with an embodiment of the present invention.

FIG. 4 is a flowchart illustrating a method 400 of the present invention in accordance with an embodiment of the present invention. The method 400 may be applied to the systems discussed with reference to FIGS. 2–3. In stage 402, an electron beam is directed at specimen, such as a semiconductor device or wafer. The electron beam may be of sufficient energy to cause electrons, such as Auger electrons, and X-ray photons to emanate from a surface of the specimen, such as discussed with reference to FIGS. 2–3.

In stages 404 and 406, the electrons and X-ray photons are detected and collected by appropriate detectors, such as those of FIGS. 2–3. For example, the electrons are detected and collected by an Auger electron detector. The X-ray photons may be detected and collected using an X-ray detector. In one embodiment, the detection of the electrons and photons occurs substantially simultaneously.

In stage 408, the electron and photon detection data may be processed and/or analyzed (e.g., by unit 212 of FIG. 2) to provide film stack characteristics, such as composition and thickness data of the film stack on the specimen of interest.

In one embodiment, since the electron detector is surface sensitive, the electron detector may be used to determine top layer composition, while the X-ray detector may be used to determine layer thicknesses and to determine the composition of layers underneath the top surface.

The Auger emission process may have higher emission probability for light elements than heavy elements. Thus, an Auger electron detector may be suitable for composition measurement, especially for light elements which compensate for the weakness of X-ray's low fluorescence yield for light elements.

One embodiment of the present invention provides a system which provides both composition and thickness information on complex film stacks which may otherwise be relatively difficult to ascertain using electron detectors and X-ray detectors as stand-alone devices.

In one embodiment, by augmenting X-ray detection only techniques with electron detection, the analysis may be made faster and hence may be more beneficial for measurement throughput improvement without sacrificing precision. In addition, electron and X-ray detection techniques may share a common electron source. Thus, the system of the present invention does not require different electron sources, which makes integration of the electron detector and the X-ray detector into one system, much easier. Accordingly, the system and method of the present invention may be done fast, in a non-destructive manner using a small spot (down to sub-micron) technique, which makes the combination an appropriate methodology used on production semiconductor devices for in-line process control.

What follows are examples of applications of an analysis system in accordance with various embodiments of the present invention.

High K Film Application

In one embodiment, with a specimen 210 having a film stack of $HfO_2/Al_2O_3/Si$, X-ray detector 202 and Auger electron detector 204 are used in conjunction to measure composition of these films. The electron beam may generate oxygen X-rays from both the $HFO_2$ layer and the $Al_2O_3$ layers. The oxygen X-ray detector 202 may measure the total X-ray emission from both layers and it may not be practical to determine, from the X-ray signal only, what fraction of X-rays came from each layer. If the top layer of $HfO_2$ is thicker than about 50 Å, the Auger electron detector 204 may measure the oxygen and Hf Auger electrons from the surface portion of the $HfO_2$ layer. This data may be used to determine the composition of this layer. Since the surface portion of the layer is sampled by Auger, it may not be practical to determine the thickness of the top layer from Auger data alone. The Hf X-ray detector may sample Hf X-rays from the entire thickness of the top layer. By combining the composition of the layer, the total Hf X-ray measurement, and a model for the density of the layer as a function of composition, a thickness may be determined for the top layer. The amount of oxygen in the top layer may be calculated from the composition and thickness and the top layer oxygen content may be subtracted from the total oxygen X-ray signal, leaving the oxygen content in the second layer as a result. The Al X-ray detector may measure the total Al content of the second layer. The total Al and O contents of the second layer, plus a model of the density as a function of composition may determine both the composition and thickness of the second layer. Alternatively, if the stoichiometric composition of $Al_2O_3$ may be assumed along with a standard density, the Al X-ray detector may be omitted and the oxygen content of the second layer directly determines the thickness. In this way the combination of the Auger and X-ray detectors may measure the thickness of both oxide layers and the composition of the $Al_2O_3$ layer from X-ray signals of Hf, Al and O at a single landing energy.

If the thickness of the top layer of $HfO_2$ is less than about 50 Å, the situation becomes more complex. The Auger detector may sample electrons from both the top and second layers. If the chemical shift is not large enough to distinguish Auger electrons from the $HfO_2$ layer from the electrons from the $Al_2O_3$ layer, it may not be practical to determine what fraction of oxygen electrons came from which layer. In this case a mathematical model may be used to obtain a measurement. The processes of electron beam penetration, ionization, Auger electron emission, X-ray emission, and Auger electron and X-ray propagation in solids may all be modeled mathematically according to basic physical principles. Modeling of this type is routinely employed for EPMA analysis and models also exist for Auger analysis. Two models for EPMA are Pouchou-Pichoir and Monte Carlo and are described in J. L. Pouchou and F. Pichoir, Electron Probe Quantization, Plenum Press, New York, 1991, pp 31–75, and J. Baro, J. Sempau, J. M. Fernandez-Varea, F. Salvat, Nuclear Instruments and Methods in Physics Research B 100 (1995) 31–46. A model for the propagation of Auger electrons may be found in W. S. M. Werner, *Surf Interf: Anal.*, 23 (1995) 737. With this method, the Auger electron and X-ray signals are estimated by the use of a mathematical model based on parameters of the film stack such as thicknesses, compositions, densities that are taken from an initial estimation. The calculated signals are compared to the measured signals and the difference is calculated. The initial film stack parameters are varied until an acceptable match is found between estimated data and measured data. Given a mathematical model, there are a variety of techniques known in the art to perform this process. These techniques include the methods of maximum likelihood (least squares) and the method of maximum entropy. Descriptions of these methods may be found in Numerical Recipes in C, $2^{nd}$ Edition, by William H. Press, Saul A. Teukolsky, William T. Vetterling and Brian P. Flannery, Cambridge University Press, 1992. Other methods such as genetic algorithms may also be used for this purpose. The parameters that generate the best match are used as the final values of the measurement. This technique may be used even in cases where the boundary of Auger emission is clear cut to improve the accuracy of the final result. All of the above mentioned references are incorporated herein by reference.

With specimens 210 having film stacks of $HfO_2/Si_3N_4/SiO_2/Si$ and $Al_2O_3/Si_3N_4/SiO_2/Si$, the oxygen signal from the $SiO_2$ layer may affect the X-ray detector results on the high K composition if the $SiO_2$ thickness is not known. Auger electron detector 204 may be used to measure oxygen from the top high K layer due to different chemical shift of the oxygen bound to Hf and bound to Si, as well as from the loss of electrons from $SiO_2$ passing through $Si_3N_4$.

Atomic Layer Deposition (ALD) Tan

For an ALD TaN barrier layer with a thickness ranging from about 5 Å to 30 Å, it may take up to more than 60 seconds for the N X-ray detector 202 to achieve the desired precision for a composition measurement, even though the Ta X-ray detector collects enough signal in 10 seconds or less. By augmenting X-ray detector 202 with Auger electron detector 204 in analysis system 200, detector 204 may detect the N signal, and therefore enable a composition measurement, with the desired high precision within a shorter measurement time.

Boron Doped SIGE Film

Because SiGeB film contains the element Si in common with the substrate, X-ray detector 202 may not be able to determine both thickness and composition from Ge and B X-ray signals. With system 200 combining X-ray detector 202 and Auger electron detector 204, the latter detector may be used to measure composition of the film (from the top surface), while X-ray detector 202 may be used to determine the film thickness from the total Ge signal.

CoWP Capping Layer for Cu Interconnect

As a capping layer for Cu interconnect, optimum CoWP films may contain a small percentage of P. Thus, X-ray detector 202 alone, may require a long acquisition time to obtain reasonably good statistics on the P X-ray signal. Auger electron detector 204 may provide a higher Auger electron yield for P than the X-ray yield, and may collect a much greater solid angle than the X-ray detector 202. Once again, the composition may be determined from the top surface of the film and the thickness may be determined from the total Co X-ray signal coupled with a model of the density as a function of composition.

Alternate Methods of Construction

Using angle resolved Auger electron spectroscopy (ARAES), a depth profile of element composition may be determined. For example, a Boron doped Ultra shallow junction (USJ) may be measured by using ARAES. Using a HSA electron spectrometer/detector is one way to implement ARAES in an efficient way since multiple angles may be collected simultaneously. Alternatively, a CMA may be scanned in angle to provide ARAES data. Additionally, two or more electron detectors may be arranged so they collect electrons at different takeoff angles.

The energy shift of Auger electron peaks may also provide chemical bonding information of elements in a film. Line shape fitting of single peak or "finger print" spectra comparison methods may be used to obtain chemical environment information from Auger electron detection data.

Although embodiments have been described in language specific to structural features and/or methodological acts, it is to be understood that claimed subject matter may not be limited to the specific features or acts described. Rather, the specific features and acts are disclosed as sample forms of implementing various embodiments. While the present invention has been described above in conjunction with one or more specific embodiments, it should be understood that the invention is not intended to be limited to one embodiment. The invention is intended to cover alternatives, modifications, and equivalents as may be included within the spirit and scope of the invention, such as defined by the appended claims.

What is claimed is:

1. A system for determining film stack characteristics of a specimen comprising:
   a beam generator configurable to direct an electron beam towards a specimen, the electron beam causing electrons and X-rays to emanate from the specimen;
   an electron detector disposed adjacent to the specimen, the electron detector configured to detect electrons and their energies emanating from at least a top layer of the specimen; and
   an X-ray detector disposed adjacent to the specimen, the X-ray detector configured to detect X-rays having characteristic energies for elements in at least one layer of the specimen.

2. The system of claim 1, further comprising an analysis unit for collecting and analyzing data resulting from the detected X-rays and electrons, wherein:
   the electron detector generates a first signal corresponding to an element and the X-ray detector generates a second signal corresponding to the element; and
   the analysis unit selects one of the first signal or the second signal to perform analysis regarding to the element.

3. The system of claim 2, wherein said analysis unit further comprises a processor linked to the beam generator and to the X-ray detector and the at least one electron detector.

4. The system of claim 1, wherein the characteristic energies may be measured simultaneously by the X-ray detector and the electron detector.

5. The system of claim 1, wherein the electron detector is configured to detect Auger electrons emanating from the specimen.

6. The system of claim 1, wherein the specimen is a semiconductor wafer.

7. The system of claim 1, wherein the electron detector comprises a cylindrical mirror analyzer.

8. The system of claim 1, wherein the beam generator comprises a scanning electron microscope.

9. The system of claim 1, wherein the electron beam is configured to penetrate at least two layers of a film stack disposed on said specimen.

10. The system of claim 1, wherein a spot size of the electron beam directed at the specimen is less than 100 microns in diameter.

11. A method for measuring at least one characteristic of a film stack on a specimen, the method comprising:
   directing an electron beam towards a specimen, such that the electron beam causes X-rays and electrons to emanate from the specimen;
   detecting electrons and their energies for at least a first layer of the film stack;
   detecting X-rays from at least one element contained in at least one layer of the film stack; and
   processing detection data resulting from the detected X-rays and electrons.

12. The method of claim 11, wherein said detecting electrons comprises detecting Auger electrons.

13. The method of claim 11, wherein detecting X-rays comprises detecting X-rays of a specific energy.

14. The method of claim 11, wherein X-rays are detected from at least one element in a layer of material underneath the first layer.

15. The method of claim 11, wherein the electrons and at least one type of X-ray may be measured simultaneously.

16. The method of claim 11, wherein the electron beam penetrates the first layer and a second layer of the film stack so that at least one characteristic of the first layer and at least one characteristic of the second layer are determined.

17. The method of claim 16, wherein the electron beam penetrates the thickness of the first layer and the second layer of the film stack so that the thickness of the first and the second layer are determined.

18. The method of claim 11, wherein the data from the electron and X-ray detectors are analyzed by a matching process to a mathematical model of the electron and X-ray emissions.

19. A system for measuring at least one characteristic of a film stack on a specimen, the system comprising:
   an electron beam configured to be directed towards a specimen, such that the electron beam causes X-rays and Auger electrons to emanate from the specimen;
   means for detecting the Auger electrons emanating from at least the top layer of the film stack;
   means for detecting X-rays emanating from at least one layer of the film stack; and
   an analysis unit for collecting data resulting from the detected X-rays and Auger electrons.

20. The system of claim 19, wherein the X-rays and Auger electrons may be detected simultaneously.

21. The system of claim 19, wherein the electron beam penetrates the top layer and at least one layer underlying the top layer of the film stack so that at least one characteristic of the top and at least one characteristic of at least one underlying layer is determined.

22. The method of claim 11, further comprising:
   generating a first signal corresponding to an element based on the detection of electrons;
   generating a second signal corresponding to the element based on the detection of X-rays; and
   selecting one of the first signal or the second signal to perform the processing.

23. The system of claim 19, further comprising:
   means for generating a first signal corresponding to an element based on the detection of electrons;
   means for generating a second signal corresponding to the element based on the detection of X-rays,
   wherein the analysis unit selects one of the first signal or the second signal to perform analysis regarding to the element.

* * * * *